United States Patent [19]
Spector et al.

[11] Patent Number: 5,939,260
[45] Date of Patent: Aug. 17, 1999

[54] METHODS OF DIAGNOSING A PREDISPOSITION FOR OSTEOARTHRITIS VIA DETECTION OF VITAMIN D RECEPTOR GENE POLYMORPHISMS

[75] Inventors: Timothy David Spector; Richard William Keen, both of London, United Kingdom

[73] Assignee: Gemini International Holdings Limited, Monaco

[21] Appl. No.: 08/845,175

[22] Filed: Apr. 21, 1997

[30] Foreign Application Priority Data

Apr. 19, 1996 [GB] United Kingdom ................. 96081336

[51] Int. Cl.$^6$ .............................. C12Q 1/68; C12P 19/34
[52] U.S. Cl. ................................. 435/6; 435/91.2
[58] Field of Search .................... 435/6, 91.2; 536/24.31, 536/24.33

[56] References Cited

U.S. PATENT DOCUMENTS

| | | | |
|---|---|---|---|
| 5,593,833 | 1/1997 | Morrison et al. | 435/6 |
| 5,698,399 | 12/1997 | Duff et al. | 435/6 |

FOREIGN PATENT DOCUMENTS

| | | |
|---|---|---|
| 0 435 362 A1 | 7/1991 | European Pat. Off. . |
| WO 94/03633 | 2/1994 | WIPO . |
| WO 95/31722 | 11/1995 | WIPO . |

OTHER PUBLICATIONS

Keen et al., Arthritis and Rheumatism 40(8), 1444–1449. (only abstract provided), 1997.
Uitterlinden et al., J. Clin. Invest. 100, 259–263, 1997.
Uitterlinden et al., J. Bone Mineral. Res. 11(9), 1241–1248. (only abstract provided), 1996.
Uitterlinden et al., Bone 20(4 Suppl.), 10S (abstract), 1997.
Brandt, K.D., and Kovalov–St. John, K., "Osteoarthritis," Chapter 281, in: *Harrison's Principles of Internal Medicine*, Twelfth Edition (International Edition), vol. 2, Wilson, J.D., et al., Eds., McGraw–Hill, Inc.; pp. 1475–1479 (1991).
Griffiths, G.O., et al., "Polymorphisms of the Vitamin D Receptor and Osteoarthritis," *British Journal of Rheumatology 35 (Suppl. 1)*:117 (May 1996).
Morrison, N.A., et al., "Contribution of trans–acting factor alleles to normal physiological variability: Vitamin D receptor gene polymorphisms and circulating osteocalcin," *Proc. Natl. Acad. Sci. USA* 89:6665–6669 (1992).
Morrison, N.A., et al., "Prediction of bone density from vitamin D receptor alleles," *Nature* 367:284–287 (1994).
Spector, T.D., et al., "Influence of vitamin D receptor genotype on bone mineral density in postmenopausal women: a twin study in Britain," *British Medical Journal* 310:1357–1360 (May 1995).

*Primary Examiner*—Kenneth R. Horlick
*Attorney, Agent, or Firm*—Sterne, Kessler, Goldstein & Fox P.L.L.C.

[57] ABSTRACT

A method of diagnosing a disease associated with a genetic polymorphism in a vitamin D receptor gene comprises determining the genotype of said vitamin D receptor gene in an animal. The method can be used to diagnose predisposition or susceptibility to osteoarthritis. Compositions for said diagnosis are provided. Methods of treatment of osteoarthritis are provided, comprising identifying an individual having a predisposition or susceptibility to the disease and subsequently treating that individual.

9 Claims, No Drawings

METHODS OF DIAGNOSING A PREDISPOSITION FOR OSTEOARTHRITIS VIA DETECTION OF VITAMIN D RECEPTOR GENE POLYMORPHISMS

BACKGROUND OF THE INVENTION

1. Field of the Invention

This invention relates to diagnostic method and apparatus based upon a polymorphism in a vitamin D receptor gene. More specifically, this invention relates to a method for diagnosis of pre-disposition or susceptibility to certain disease states, by screening for the presence of this polymorphism. The invention also relates to compositions for screening for the polymorphism.

2. Related Art

Osteoarthritis, or degenerative joint disease as it is also known, is one of the most common types of arthritis. It is characterised by the breakdown of the joint's cartilage, causing bone to rub against bone causing pain and loss of movement. Osteoarthritis can range from very mild to very severe and most commonly affects middle-aged and older people. It affects hands and weight-bearing joints, such as the knees, hips, feet and back.

Although age is a leading risk factor, at present the aetiology and pathogenesis of this condition remain largely unknown. Many environmental factors and other independent conditions have been associated with osteoarthritis, including obesity, previous injury and/or meniscectomy, knee bending occupations, smoking, sex hormones, gynaecological disorders and other metabolic factors. Obesity may lead to osteoarthritis of the knees. Also, people with injuries to the joints because of sports, repeated movements, or accidents may be at increased risk of developing osteoarthritis.

At present accurate diagnosis of osteoarthritis is in general possible only when the disease has progressed significantly. Physicians can do little more than make a diagnosis of osteoarthritis based on a physical examination and history of symptoms. X-ray is typically used only to confirm diagnosis.

A recent study concluded that weight loss in middle-aged people who are overweight can significantly reduce the risk or even prevent knee osteoarthritis from developing. In such cases an ability to improve accuracy of diagnosis of predisposition or susceptibility to osteoarthritis would be of distinct advantage.

BRIEF SUMMARY OF THE INVENTION

It is an object of the present invention to improve diagnosis of osteoarthritis. It is a particular object of the invention to provide a method of diagnosis of predisposition or susceptibility to osteoarthritis. A further object is to provide, following such diagnosis, a method of preventative or palliative therapy for osteoarthritis before the disease becomes significantly established. Another object is to provide means for diagnosing predisposition or susceptibility to osteoarthritis.

Other preferred embodiments of the present invention will be apparent to one of ordinary skill in light of the following description of the invention and of the claims.

DETAILED DESCRIPTION OF THE INVENTION

In a first aspect, the invention provides a method of diagnosing a disease associated with a genetic polymorphism in a vitamin D receptor gene in an animal predisposed or susceptible to said disease, said method comprising determining the genotype of said vitamin D receptor in said animal. The first aspect of the invention further provides a method of identifying an animal predisposed or susceptible to a disease associated with a genetic polymorphism in a vitamin D receptor gene, said method comprising determining the genotype of said vitamin D receptor gene in said animal.

According to an embodiment of the first aspect of the invention there is provided a method of diagnosis of predisposition or susceptibility to osteoarthritis comprising determining genotype of a vitamin D receptor gene of an individual. Typically, the method comprises determining whether an individual is homozygous or heterozygous for alternative versions of a vitamin D receptor gene. In an embodiment of the invention, the method of diagnosis is to screen for an individual at risk of a condition or disease such as osteoarthritis correlated with a vitamin D receptor gene polymorphism.

The invention is based upon the observation of a correlation between polymorphisms in the vitamin D receptor gene, specifically in exon 9 of this gene and in the region from exon 7 to the 3'UTR, and predisposition or susceptibility to osteoarthritis. The invention is of advantage in that by screening for the presence of the polymorphism it is possible to identify individuals likely to have a genetic predisposition or susceptibility to the disease.

In an embodiment of the invention diagnosis is carried out by determining whether a fragment of the vitamin D receptor gene contains a cleavage site for restriction enzyme TaqI. An individual is typically then classified according to whether the fragment contains a cleavage site for TaqI, wherein possessing a fragment that contains the cleavage site correlates with decreased risk of predisposition or susceptibility to osteoarthritis.

Thus, a vitamin D receptor gene in which the TaqI cleavage site is absent can be classified as a risk polymorphism of the gene, that is to say a polymorphic variant of the gene that is correlated with increased risk of predisposition or susceptibility to osteoarthritis. As a human genome contains two vitamin D receptor genes, one on each of a pair of chromosomes, an individual can accordingly be found to be homozygous or heterozygous for the risk polymorphism, or to lack the risk polymorphism.

In a further embodiment of the invention the method comprises determining whether a fragment of the vitamin D receptor gene contains a cleavage site for restriction enzyme BsmI. An individual is classified according to presence or absence of the cleavage site, wherein being homozygous for absence of the cleavage site correlates with decreased risk of predisposition or susceptibility to osteoarthritis. In this embodiment, a polymorphism of the gene in which the BsmI cleavage site is present is a risk polymorphism of the gene.

In a still further embodiment of the invention, the method comprises determining whether a fragment of the vitamin D receptor gene contains a cleavage site for restriction enzyme ApoI. An individual's risk of predisposition or susceptibility to osteoarthritis is classified as increased when the gene contains a cleavage site for ApoI, and being homozygous for presence of the cleavage site indicates an individual likely to be at increased risk.

The method conveniently comprises amplifying a fragment of a vitamin D receptor to produce copies and determining whether copies of the fragment contain a cleavage site for one of the restriction enzymes TaqI, BsmI or ApoI.

The method optionally includes testing the vitamin D receptor genotype using more than one or these restriction enzymes, or all of them.

A suitable technique is to amplify the fragment using PCR techniques, producing copies of a fragment that is at least 500 base pairs in length, preferably at least 600 base pairs in length. It is preferred that the PCR primers are selected so as to amplify a region of the gene that is about 740 base pairs in length. PCR techniques are well known in the art and it would be within the ambit of a person of ordinary skill in this art to identify primers for amplifying a suitable section of exon 9 of the vitamin D receptor gene. PCR techniques are described for example in EP-A-0200362 and EP-A-0201 184. In a further embodiment of the invention, the diagnostic method comprises analysis of the vitamin D receptor gene using single strand conformational polymorphism (SSCP) mapping to determine whether the vitamin D receptor gene is the risk or the non-risk form.

In a specific embodiment of the invention, described in an example below, diagnosis is carried out comprising amplifying a fragment of exon 9 of a vitamin D receptor gene, in particular a fragment that is about 740 base pairs in length. Alternatively, the method uses other methods of analysis of the genotype of an individual to determine whether the fragment contains a cleavage site for TaqI.

Suitable PCR primers are:

[SEQ ID NO:1] 1: CAGAGCATGGACAGGGAGCAAG (3')

[SEQ ID NO:2] 2: GCAACTCCTCATGGCTGAG-GTCTC (3')

wherein the amplified fragment is about 740 base pairs in length. Using these primers, a fragment of DNA is amplified and tested for whether a TaqI cleavage site is present. The site is present for example where a ATT codon in exon 9 has been changed to ATC.

In further specific embodiments of the invention, the method comprises determining genotype of a region of a vitamin D receptor gene from exon 7 to the 3'UTR, using either BsmI or ApoI. The methods comprises amplifying the specified region and testing for presence or absence of a cleavage site for restriction enzyme BsmI or ApoI, prescence of the cleavage site being the risk genotype.

A further embodiment of the method of the invention, for diagnosis of predisposition or susceptibility to osteoarthritis in an individual, comprises determining whether the individual possesses a risk related polymorphic version of a vitamin D receptor gene, a risk related polymorphic version of the gene being one that lacks a cleavage site for restriction enzyme TaqI, the method comprising (a) using PCR techniques to amplify a fragment of exon 9 of the vitamin D receptor gene to make copies of the fragment, (b) testing whether the copies contain a cleavage site for TaqI, and thereby determining whether the individual is homozygous or heterozygous for a polymorphic version of the gene, and (c) diagnosing that individual's risk of predisposition or susceptibility to osteoarthritis as greatest if that individual is homozygous for the polymorphic version of the gene and least if that individual lacks the polymorphic version.

In an example of the invention, the PCR primers:

[SEQ ID NO:2] 1:CAGAGCATGGACAGGGAGCAAG

[SEQ ID NO:2] 2: GCAACTCCTCATGGCTGAG-GTCTC are used to amplify a 740 base pair fragment of exon 9 of a vitamin D receptor gene.

As described above, in preferred embodiments of the first aspect of the invention, the method comprises screening a vitamin D receptor gene, and this screening is conveniently carried out by any one of a number of suitable techniques that are known in the art, and may be conveniently selected from amplification of a nucleic acid sequence located within the vitamin D receptor gene, Southern blotting of regions of the gene and single strand conformational polymorphism mapping of regions within the gene. The genotype in that region is also optionally determined using hybridisation probes adapted selectively to hybridise with a particular polymorphism of the vitamin D receptor gene which is associated with predisposition or susceptibility to disease.

A probe used for hybridisation detection methods must be in some way labelled so as to enable detection of successfully hybridisation events. This is optionally achieved by in vitro methods such as nick-translation, replacing nucleotides in the probe by radioactively labelled nucleotides, or by random primer extension, in which non-labelled molecules act as a template for the synthesis of labelled copies. Other standard method of labelling probes so as to detect hybridisation are know to those skilled in this art.

According to a second aspect of the invention there is provided a method of diagnosis and therapy comprising diagnosing predisposition or susceptibility to osteoarthritis according to the method of the first aspect of the invention and treating an individual having such a predisposition or susceptibility to prevent or lessen osteoarthritis.

Known therapies for osteoarthritis can be effective in halting advancement of the disease, or at least slowing the advancement. Such existing therapies are generally not, however, able to bring about a dramatic reversal of the disease state, that is to say it are not capable of inducing a significant lessening of pain and discomfort for sufferers. It is thus an advantage of the invention that early diagnosis of osteoarthritis is improved, so that preventative therapy can be started. As alternative diagnostic methods improve and are developed, so the invention can add to the total knowledge of the risk of developing osteoarthritis of an individual. The decision of a physician on how and whether to initiate therapy in anticipation of the disease can be taken with increased confidence.

Suitable treatments for use in the invention comprise prescribing osteoarthritis preventative or palliative therapy, such as exercise to keep joints flexible, exercise to improve muscle strength, use of joint protection to prevent strain or stress on joints, weight control to prevent stress on weight bearing joints and surgery to prevent or control joint stress. Suitable pharmaceutical treatments include the use of symptom modifying agents or disease modifying agents.

A variety of suitable treatments of osteoarthritis are described in the art, and the contents of these are incorporated herein by reference. WO-A-97/00675 describes the use of anthraquonine compounds for treatment of osteoarthritis, and U.S. Pat. No. 5,591,740 describes treatment of osteoarthritis using 3,4-azepinyl-pyrrole derivatives. A dermatological preparation for treatment of osteoarthritis is described in JP-A-08/169832. WO-A-96/18403 describes a further composition for treatment of osteoarthritis, comprising diclofenac sodium and trebenoside. Other pharmaceutical treatments for osteoarthritis are described in WO-A-96/09043 and JP-A-08/053403. A medial collateral ligament brace for medical treatment of knee ligament damage and osteoarthritis is described in U.S. Pat. No. 5,562,605. Other treatments will be known to persons of skill in the art.

A third aspect of the invention provides a composition for use in diagnosing a disease associated with a genetic polymorphism in a vitamin D receptor gene in an animal predisposed or susceptible to said disease, said composition comprising one or more primer nucleic acid molecules adapted to amplify a portion of a vitamin D receptor gene selected from a portion of exon 9 and a portion of the gene between exon 7 and the 3'UTR.

A third aspect of the invention also provides a composition for use in identifying an animal predisposed or susceptible to a disease associated with a genetic polymorphism in a vitamin D receptor gene, said compositions comprising one or more primer nucleic acid molecules adapted to amplify a portion of the vitamin D receptor gene selected from a portion of exon 9 and a portion between exon 7 and the 3'UTR.

In an embodiment of the invention, the composition of the third aspect of the invention comprises a nucleic acid molecule capable of identifying a polymorphism in said vitamin D receptor gene, said polymorphism being indicative of a risk genotype in said animal.

A further embodiment of the third aspect of the invention provides a composition for diagnosis of predisposition or susceptibility to osteoarthritis, comprising means for determining genotype of a vitamin D receptor gene of an individual, for example whether an individual is homozygous or heterozygous for polymorphic variants of a vitamin D receptor gene.

In an embodiment of the invention a diagnostic composition comprises PCR primers adapted to amplify a DNA sequence within exon 9 of a vitamin D receptor.

A diagnostic composition according to a further embodiment of the invention comprises PCR primers adapted to amplify a DNA sequence within exon 9 of a vitamin D receptor gene, wherein alternative versions of the gene are distinguished one from another by whether said sequence contains or lacks a site for cleavage by restriction enzyme TaqI. Suitable PCR primers are:

[SEQ ID NO:1] 1: CAGAGCATGGACAGGGAGCAAG (3')

[SEQ ID NO:2] 2: GCAACTCCTCATGGCTGAG-GTCTC (3')

Additionally, the diagnostic composition according to the invention can contain a supply of restriction enzyme TaqI.

In a fourth aspect of the invention there is provided a diagnostic kit comprising a diagnostic composition as described above and an indicator composition for indicating how possessing a polymorphic version of a vitamin D receptor gene correlates with predisposition or susceptibility to osteoarthritis.

Diagnostic kits are typically accompanied by or comprise a chart or other visual aid for assistance in interpreting the results obtained using the kit. Suitable indicator compositions for use in the diagnostic kit of the invention include a leaflet or other visual reminder that possessing the risk polymorphism version of a vitamin D receptor gene correlates with increased risk of predisposition or susceptibility to osteoarthritis.

In a still further aspect of the invention there is provided use, in the manufacture of means for diagnosing whether an individual has a predisposition or susceptibility to osteoarthritis, of PCR primers adapted to amplify a region of exon 9 in a vitamin D receptor gene. Alternative versions of the gene are typically distinguished one from another by whether said region contains a site of cleavage by TaqI. Suitable PCR primers are:

[SEQ ID NO:1] 1: CAGAGCATGGACAGGGAGCAAG (3')

[SEQ ID NO:2] 2: GCAACTCCTCATGGCTGAG-GTCTC (3')

According to the invention, an individual who is homozygous for a risk polymorphism, that is to say homozygous for a version of the gene which is free of a TaqI cleavage site in exon 9, is classified as being at highest risk. An individual being heterozygous is classified as having moderate risk.

Optionally, the assessment of an individual's risk factor according to any aspect of the invention is calculated by determining the genotype of a vitamin D receptor gene polymorphism and combining the result with analysis of other known genetic or physiological or dietary or other indications. The invention in this way provides further information on which measurement of an individual's risk can be based.

In exercise of a specific embodiment of the invention, described in detail below, an association has been demonstrated between a vitamin D receptor gene polymorphism and early knee osteoarthritis in women from the general population. In the specific embodiment of the invention, the risk polymorphism has been indicated as T, and absence of the risk polymorphism as t. The TT genotype is over represented in women with knee osteoarthritis compared to the tt genotype and appears to offer a 4-fold risk of development of this disease state when compared to the alternate homozygous genotype tt. This relationship can not be explained on the basis of age, as no significant deviation from expected genotype frequencies in the total group after stratification by age was observed. A secular alteration in population structure due to either migration or immigration in the 1930's–40's or premature death which could both have altered the genotype frequencies is therefore unlikely.

Although knee osteoarthritis has been suspected to be under genetic influence, no candidate genes have hitherto been reported. The vitamin D receptor locus maps to chromosome 12q12-14 by somatic cell hybridisation. The TaqI polymorphism represents a synonymous codon change is exon 9 of the vitamin D receptor gene, and therefore does not alter the receptor's protein structure. It is possible that vitamin D receptor polymorphisms are not the disease causing genes but are instead in linkage disequilibrium with a nearby novel disease susceptibility gene on chromosome 12. Nevertheless, the observed correlation is of use in diagnosis of risk of predisposition or susceptibility to osteoarthritis.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following example, which is included herewith for purposes of illustration only and is not intended to be limiting of the invention.

EXAMPLE 1

Relationship Between Vitamin D Receptor Polymorphisms and Osteoarthritis

Patients and Methods

The study design was a nested case-control study within a population cohort of 1003 women, with a mean age (±SD) of 54.2±6.0 years. Women in the age range 45–64 had been selected from a large single general practice in Chingford, North-East London (total of 11,000 registered patients) to participate in a longitudinal epidemiological study of rheumatic diseases. 1,353 women were found to be in the age range specified, and of these 78% (1,003) agreed to participate. The area is predominantly middle class, 98% are white and the population similar to UK normals in terms of height, weight, smoking status, hysterectomy rates and use of hormone replacement therapy (HRT) (Hart D J, Spector T D: The relationship of obesity, fat distribution and osteoarthritis in the general population: the Chingford Study. J Rheumatol 20:331–335, 1993). Women were selected for this study on the basis of postmenopausal status, which was defined by absence of menstruation for 12 months and confirmed by measurement of sex hormones (serum estradiol, luteinising hormone and follicular stimulating hormone). All women completed an extensive questionnaire detailing risk factors for both osteoporosis and OA. The study was approved by the Local Ethics Committee and all women gave informed consent to participate.

Antero-posterior weight bearing knee radiographs were performed using standard procedures and subsequently graded blind by a single observer (DJH) according to the methods of Kellgren & Lawrence where a scale of 0 to 4 is used (0 representing no disease and 4 representing severe disease) (Kellgren J H, Lawrence J S: The Epidemiology of Chronic Rheumatism. Oxford: Blackwell Scientific, 1963). Radiological definition of OA is the currently accepted standard for epidemiological studies of OA in populations (Spector T D, Hart D J, Byrne J, Harris P A, Dacre J E, Doyle D V: Definition of osteoarthritis of the knee for epidemiological studies. Ann Rheum Dis 52:790–794, 1993). Knee OA was defined as present if a grade of 2 or more was given, and controls were classified as having no OA with a grade of 1. The intra-observer reproducibility for this technique was good with a kappa score of over 0.8. Presence of Heberden's nodes was determined by clinical hand examination (Egger P, Cooper C, Hart D J, Doyle D V, Coggon D, Spector T D: Patterns of joint involvement in osteoarthritis of the hand. J Rheumatol 22:1509–1513, 1995). BMD was measured at the femoral neck using dual energy xray absortiometry with a Hologic QDR-1000 (Hologic Inc., Waltham, Mass.). Reproducibility (CV %), assessed by duplicate measures in healthy volunteers, was 1.4% at the femoral neck.

DNA was extracted from peripheral blood leucocytes using standard techniques. PCR was used to amplify a 740 bp fragment of the VDR gene using published primers and reaction conditions (Spector T D, Keen R W, Arden N K, Morrison N A, Major P J, Nguyen T V, Baker J R, J R Baker, Sambrook P N, Lanchbury J S, Eisman J A:. Vitamin D receptor gene (VDR) alleles and bone density in postmenopausal women: a UK twin study. BMJ 310: 1357–1360, 1995; Morrison N A, Qi J C, Tokita A, Kelly P J, Crofts L, Nguyen T V, Sambrook P N, Eisman J A:. Prediction of bone density from vitamin D receptor alleles. Nature 367: 284–287, 1994) VDR genotypes were obtained by digestion of the PCR product with the restriction enzyme TaqI (Promega Corps) and alleles were coded as "T" (absence of TaqI restriction site) and "t" (presence of restriction site). Differences in demographic variables between OA cases and controls, and between VDR genotypes were initially compared using analysis of variance and chi-squared test. VDR genotype frequencies were compared between OA and control groups using Fishers exact test. Conditional logistic regression analysis was used to estimate the odds ratio and 95% test based confidence intervals for developing a radiological feature of OA for the individual VDR genotypes, with the homozygous VDR genotype "tt" set as baseline. Adjustment for other potential confounding variables was performed using conditional logistic regression with the PC software statistical programme STATA.

Results

In total, 501 women from the total cohort were postmenopausal and had graded knee radiographs. Full genotype results were available on 351 (70%) women: 82 subjects with knee OA and 269 with normal radiographs. The mean age ±SD for the total group of 351 women was 55.3±5.0 years. Subdivision of women with genotype results according to their radiological grading for OA showed that of the cases, 63 (76.8%) were grade 2, 15 (18.3%) grade 3 and 4 (4.9%) grade 4. For controls, 201 (74.7%) were grade 0 and 68 (25.3%) grade 1. The characteristics of the women according to the absence or presence of knee OA are shown in Table 1, and are similar to those of the whole cohort except for age, menopause status and duration. No significant differences were observed between subjects with genotype results and those where DNA was unavailable. Within the 351 women with full results, there were significant differences between the cases and controls for potential confounders such as age, body mass index (BMI), use of HRT, and hip BMD.

VDR genotype frequencies in the total group of 351 women were similar to those reported in other Caucasian populations and in Hardy Weinberg equilibrium (Spector T D, Keen R W, Arden N K, Morrison N A, Major P J, Nguyen T V, Baker J R, J R Baker, Sambrook P N, Lanchbury J S, Eisman J A:. Vitamin D receptor gene (VDR) alleles and bone density in postmenopausal women: a UK twin study. BMJ 310: 1357–1360, 1995; Morrison N A, Qi J C, Tokita A, Kelly P J, Crofts L, Nguyen T V, Sambrook P N, Eisman J A:. Prediction of bone density from vitamin D receptor alleles. Nature 367: 284–287, 1994). There were no significant differences in the baseline characteristics as measured in Table 1 between the VDR genotypes within this total group or after stratification by Kellgren and Lawrence OA grade. The frequencies of the TaqI genotypes were found to differ significantly between the OA cases and controls using Fisher's exact test (P=0.03) with the tt genotype frequency being reduced with worsening OA status, although the number of subjects with severe OA (grade 3) was too small for formal analysis (Table 2).

TABLE 1

Demographic Variables of Women and their Knee OA Status (mean ± SD unless indicated)

| | Controls | | | OA Cases | | | |
| --- | --- | --- | --- | --- | --- | --- | --- |
| Variable | Total (n = 269) | Grade 0 (n = 201) | Grade 1 (n = 68) | Total (n = 82) | Grade 2 (n = 63) | Grade 3 (n = 15) | Grade 4 (n = 4) |
| Age (yrs) | 54.4 (4.8) | 54.1 (4.8) | 55.4 (4.6) | 58.3* (4.7) | 58.1 (4.6) | 58.1 (5.2) | 62.5 (1.9) |

TABLE 1-continued

Demographic Variables of Women and their Knee OA Status (mean ± SD unless indicated)

| | | Controls | | | OA Cases | | |
|---|---|---|---|---|---|---|---|
| Variable | Total (n = 269) | Grade 0 (n = 201) | Grade 1 (n = 68) | Total (n = 82) | Grade 2 (n = 63) | Grade 3 (n = 15) | Grade 4 (n = 4) |
| BMI (kg/m$^2$) | 25.0 (3.6) | 24.5 (3.5) | 26.2 (3.8) | 28.0* (4.0) | 27.7 (3.7) | 28.4 (4.5) | 30.8 (4.9) |
| Age at menopause (yrs) | 47.8 (5.0) | 47.9 (4.9) | 47.1 (5.3) | 47.7 (4.7) | 47.7 (4.8) | 48.1 (4.8) | 46.5 (4.1) |
| Ever use of HRT (n, %) | 78 (29%) | 57 (28%) | 21 (31%) | 15† (18%) | 10 (16%) | 5 (33%) | 0 (0%) |
| Ever smokers (n, %) | 112 (42%) | 83 (41%) | 29 (43%) | 37 (45%) | 29 (46%) | 6 (40%) | 2 (50%) |
| BMD Femoral neck (g/cm$^2$) | 0.73 (0.12) | 0.73 (0.11) | 0.75 (0.12) | 0.77‡ (0.13) | 0.77 (0.14) | 0.78 (0.10) | 0.72 (0.08) |

*P < 0.001 (cases vs controls)
†P = 0.05 (cases vs controls)
‡P = 0.008 (cases vs controls)

TABLE 2

VDR Genotype Frequecies (n, %) according to Kellgren and Lawrence OA Grade

| | Grade 0 (n = 201) | Grade 1 (n = 68) | Grade 2 (n = 63) | Grade 3 (n = 15) | Grade 4 (n = 4) |
|---|---|---|---|---|---|
| TT | 74 (36.8%) | 24 35.3%) | 19 (30.2%) | 10 (66.7%) | 0 (0%) |
| Tt | 87 (43.3%) | 36 (52.9%) | 38 (60.3%) | 4 (26.7%) | 4 (100%) |
| tt | 40 (19.9%) | 8 (11.8%) | 6 (9.5%) | 1 (6.6%) | 0 (0%) |

The frequency of the T allele was increased by 5% in the OA group compared to controls, although this difference was non-significant. The odds ratios (95% CI) for knee OA in the "TT" VDR genotype group compared to the alternate homozygous genotype "tt" was 2.42 (0.94–6.21, p=0.07), and in the heterozygous genotype Tt 3.15 (1.26–7.83, p=0.01) (Table 3). After adjustment for variables judged to be potential confounders (age, BMI, HRT use and hip BMD), the odds ratio for knee OA (95% CI) in those with the TT genotype (TT vs tt) remained marginally increased at 2.82 (0.98–8.10, p<0.05). After similar adjustment the odds ratio for the "Tt" genotype (Tt vs tt) was marginally reduced at 2.98 (1.09–8.12, p=0.03). As risk of knee OA appeared to be associated with presence of the T allele with a dominant inheritance pattern, analysis was subsequently performed on the genotypes TT and Tt combined against the tt homozygous group set at baseline. Crude analysis showed an odds ratio of 2.82 (1.16–6.85, p=0.02) for risk of knee OA in association with the T allele. This increase in risk remained after adjustment as previously detailed with an odds ratio of 2.60 (1.01–6.71, p<0.05).

No significant relationship was observed between VDR genotype and nodal arthritis, as determined by the presence of Heberden's nodes. In addition there was no difference in genotype frequencies in the subset of knee OA cases who also had clinical nodes present compared to knee OA alone (data not shown). Within the total group of 351 women we were also not able to demonstrate any overall significant relationship between BMD and VDR genotype, although there was a 4.6% difference in BMD at the hip between the homozygous genotypes TT and tt. Adjustment for potential confounders such as age, BMI, HRT use and OA grade did not appreciably alter these findings.

TABLE 3

Effect of VDR Genotype on Risk of Knee OA - Odds Ratio (95% Confidence Interval) Crude and Adjusted

| VDR Genotype | Frequency in OA cases (%) | Frequency in controls (%) | OR (Crude) | OR (Adjusted*) |
|---|---|---|---|---|
| TT | 29 (35.4%) | 98 (36.4%) | 2.42 (0.94, 6.21) | 2.82 (0.98, 8.10) |
| Tt | 46 (56.1%) | 123 (45.7%) | 3.15 (1.26, 7.83) | 2.98 (1.09, 8.12) |
| tt | 7 (8.5%) | 48 (17.9%) | 1.0 | 1.0 |

*Adjusted for age, BMI, femoral neck BMD, use of HRT

Discussion

Our data demonstrate an association between a TaqI polymorphism of the VDR locus and early knee OA in women from the general population. The "T" allele is associated with a nearly 3-fold increased risk for development of knee OA when compared to the alternate allele. The pattern of risk was observed to be codominant, with the homozygous genotype TT and the heterozygous genotype Tt both having an equivalent increased risk of knee OA. This relationship cannot be explained on the basis of age, as we observed no significant deviation from expected genotype frequencies in the total group after stratification by age. This relationship was also independent of other factors such as BMI, HRT use and bone mineral density which have been shown to influence OA risk and were found to differ between the cases and controls. Our finding that there was no relationship between the VDR locus and nodal arthritis suggests that differing genetic mechanisms may underlie the development of Heberdens nodes and associated generalised osteoarthritis.

The invention thus provides method and apparatus for diagnosis and treatment of individuals having a predisposition or susceptibility to osteoarthritis, by determining the genotype of the individual in respect of the vitamin D receptor gene. Early diagnosis or improved diagnosis enables an individual to receive preventative or palliative treatment at a time when this treatment can be effective.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

3. The method of claim 1 or claim 2 comprising determining whether an individual is homozygous or heterozygous for alternative versions of a vitamin D receptor gene.

4. The method of claim 3 comprising determining whether a fragment of the vitamin D receptor gene contains a cleavage site for a restriction enzyme selected from the group consisting of TaqI, BsmI and ApoI.

5. The method of claim 4 comprising amplifying a fragment of exon 9 of a vitamin D receptor gene or a region from exon 7 to the 3'UTR of the gene.

6. The method of claim 5 further comprising classifying an individual according to whether the fragment contains a

What is claimed is:

1. A method of diagnosing osteoarthritis associated with a genetic polymorphism in a vitamin D receptor gene in an animal predisposed or susceptible to osteoarthritis, said method comprising determining the genotype of said vitamin D receptor gene in said animal, and diagnosing osteoarthritis based on said genotype.

2. A method of identifying an animal predisposed or susceptible to osteoarthritis associated with a genetic polymorphism in a vitamin D receptor gene, said method comprising determining the genotype of said vitamin D receptor gene in said animal, and identifying said animal based on said genotype.

cleavage site for TaqI, wherein possessing a fragment that lacks the cleavage site correlates with increased risk of predisposition or susceptibility to osteoarthritis or whether the region contains a cleavage site for BsmI or ApoI, wherein possessing a region that contains the cleavage site correlates with increased risk.

7. The method of claim 6 wherein the fragment is amplified using the PCR primers:

[SEQ ID NO:1] 1: CAGAGCATGGACAGGGAGCAAG (3') and

[SEQ ID NO:2] 2: GCAACTCCTCATGGCTGAG-GTCTC (3').

8. A method of diagnosis of predisposition or susceptibility to osteoarthritis in an individual, the method comprising determining whether the individual possesses a polymorphic risk version of a vitamin D receptor gene, a polymorphic risk version of the gene being one that does not contain a cleavage site for restriction enzyme TaqI, the method comprising (a) using PCR techniques to amplify a fragment of exon 9 of the vitamin D receptor gene to make copies of the fragment, (b) testing whether the copies contain a cleavage site for TaqI, and thereby determining whether the individual is homozygous or heterozygous for a polymorphic risk version of the gene, and (c) diagnosing that individual's risk of predisposition or susceptibility to osteoarthritis as greatest if that individual is homozygous for the polymorphic risk version of the gene and least if that individual lacks the polymorphic risk version.

9. The method of claim 8 comprising using the PCR primers:

[SEQ ID NO:1] 1: CAGAGCATGGACAGGGAGCAAG (3') and

[SEQ ID NO:2] 2: GCAACTCCTCATGGCTGAG-GTCTC (3')

to amplify a 740 base pair fragment of exon 9 of a vitamin D receptor gene.

* * * * *

UNITED STATES PATENT AND TRADEMARK OFFICE
CERTIFICATE OF CORRECTION

PATENT NO. : 5,939,260
DATED : August 17, 1999
INVENTOR(S) : Spector et al.

Page 1 of 1

It is certified that error appears in the above-identified patent and that said Letters Patent is hereby corrected as shown below:

<u>Title page,</u>
Assignee, please delete "Gemini International Holdings Limited, Monaco" and insert therefor -- Gemini Research Ltd., Cambridge, England --.

Signed and Sealed this

Fifth Day of February, 2002

*Attest:*

JAMES E. ROGAN
*Director of the United States Patent and Trademark Office*

*Attesting Officer*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

CAGAGCATGG ACAGGGAGCA AG

22

(2) INFORMATION FOR SEQ ID NO: 2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 2:

GCAACTCCTC ATGGCTGAGG TCTC

24